Jan. 2, 1962 L. A. LAMBOROT Plant Pat. 2,118
CHRYSANTHEMUM PLANT
Filed March 30, 1960
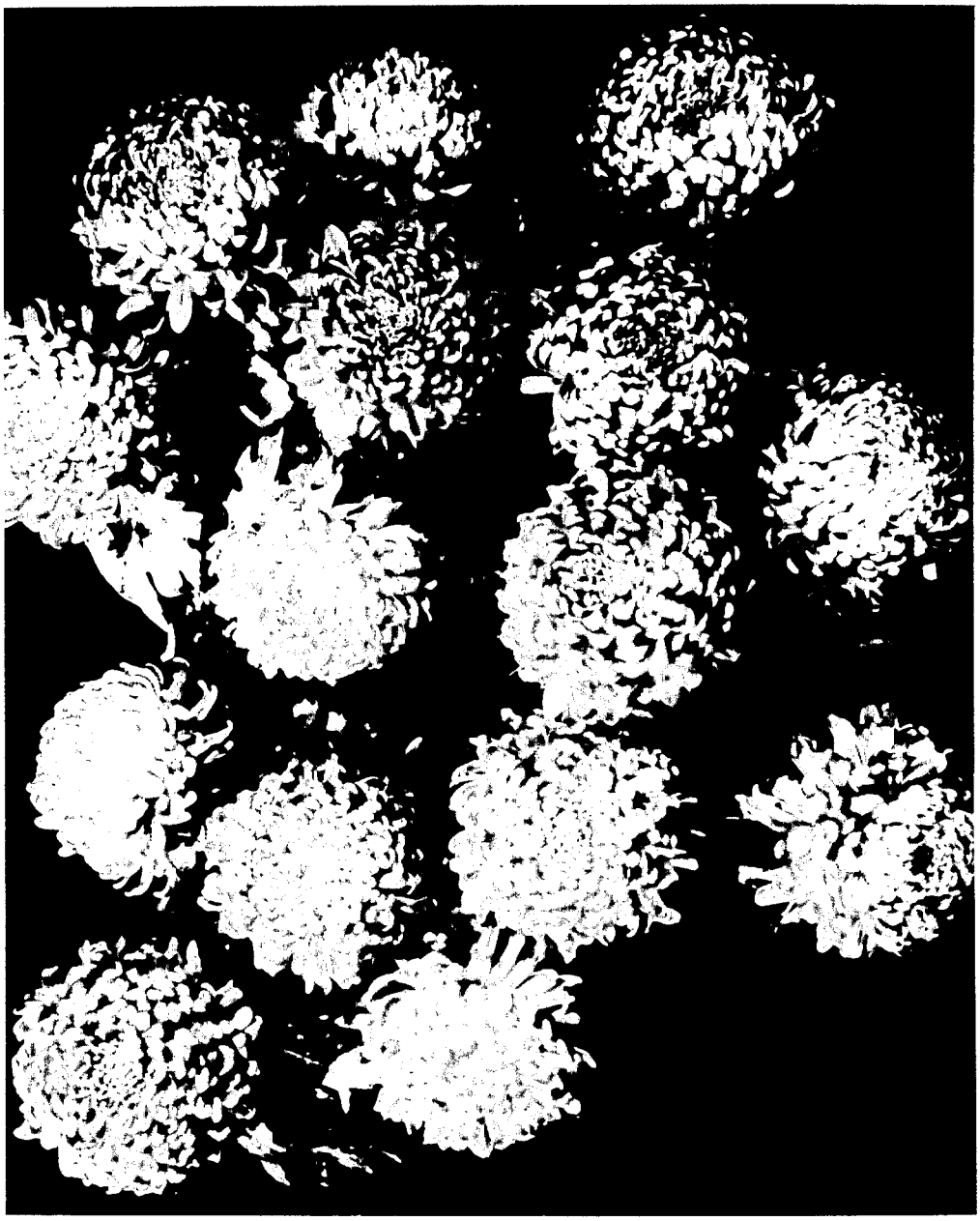
Inventor
L. A. Lamborot
by Robb & Robb
attorneys United States Patent Office Plant Pat. 2,118
Patented Jan. 2, 1962

2,118
CHRYSANTHEMUM PLANT

Lazare Antoine Lamborot, Montceau les Mines, France, assignor to George J. Ball, Inc., West Chicago, Ill., a corporation of Illinois Filed Mar. 30, 1960, Ser. No. 18,793
1 Claim. (Cl. 47—60)

My present invention comprises a new and distinct variety of chrysanthemum plant, being a seedling, and which seedling is the result of crossing the variety No. 55–57 (unpatented) which is a variety of my own production, with the unpatented variety which I have designated No. 54–2.

The object of this invention has been to produce a new variety of chrystanthemum of the *morifolium* type which will have a more striking color than similar varieties, more closed center when the bloom is mature, and be less tall in its habit of growth than such similar varieties.

This present new variety is the result of careful selection and cross-breeding of various plants to develop more showy, bright blooms, with stronger stems and a more uniform habit of growth than comparable varieties.

More specifically stated I have continuously conducted a program of hybridization and as a result have produced a large number of different plants, and in this instance have selected the specific plants designated as the parents of the new variety, the seed parent in this particular instance being a variety which is as indicated previously designated by the number 55–57. The pollen parent is another variety of mine which is designated by number only at No. 54–2.

The result of the specific hybridization previously referred to has been to produce my present new and distinct variety of chrysanthemum plant, characterized by the very large, more closed center and strong reddish orange tinted with reddish orange color of its blooms, the very double arrangement of its petals, its short, strong stems, its better habit and profuse bloom through the blooming period is intermittent.

More specifically, the blooms of my new variety are of the strong reddish orange color, tinted with reddish ornage (Nickerson Color Fan, published by Munsell Color Company). As grown in the vicinity of Montceau les Mines, France, under uniform culture, the plants of my new variety have grown in compact bushes, with large abundant foliage.

My new variety appears to have quite a number of characteristics of both of the parent varieties, but better characteristics than eitehr separately and my new variety differs from both of its parents and from other known varieties in many respects.

In comparing the color of the bloom of my new variety with the color of the blooms of the variety "Delaware" (unpatented), it is to be noted that my new variety is not as dark red in color, and the center of my new variety is less open.

My new variety is also an improvement over the variety "Woking Scarlet" (unpatented), since the latter has a tendency to grow tall with weak stems, which my new variety improves upon by having shorter stronger stems.

Another variety, somewhat similar to my new variety, and known as "Bronze Calypso" (unpatented), has weak stems and tends to develop a non uniform, straggly plant, in contrast to my new variety which produces strong, compact and substantially uniform stems.

Under the conditions of culture previously mentioned which have been undertaken in the region of Montceau les Mines, France, plants of my new variety have shown vigorous growth, somewhat more compact form and slightly more dwarf than similar varieties.

My new variety has been asexually reproduced by cuttings in the vicinity of Montceau les Mines, France, and found to retain its distinctive characteristics through such reproduction.

The accompanying drawing forming a part hereof shows a typical plant of my new variety of chrysanthemum.

The following is a detailed description of my new variety of chrysanthemum plant, the color references being to the Nickerson Color Fan, published by Munsell Color Company:

Parentage: Seedling.
- *Seed parents.*—55–57 (unpatented).
- *Pollen parent.*—54–2 (unpatented).

Classification: Botanic: *Chrysanthemum morifolium.*

Blooming habit: Blooms profusely in mid-fall and intermittently.

Bud:
- *Size.*—Large.
- *Form.*—Short with flat top. Not affected by hot or wet weather.
- *Color.*—When sepals first divide—between 2.5YR 6/12, strong orange, and 5YR 7/11 strong orange. When petals begin to unfurl—7.5YR 7/11, strong orange. When half blown, inside of petals—between 7.5R 5/13, strong reddish orange, and 7.5R 5/11, dark reddish orange. When half blown, reverse of petals—between 10YR 8/10, moderate orange yellow, and 10YR 7/10, strong orange yellow.
- *Sepals.*—Smooth edge.
- *Calyx.*—Shape—funnels. Size—small. Aspect—mossy. Odor when rubbed—typical chrysanthemum odor.
- *Peduncle.*—Length—short. Aspect—rough. Color—medium green. Strength—stiff. Bud opens well. Not affected by adverse conditions.

Bloom:
- *Size.*—Very large. Average size when fully expanded—5½ inches.
- *Borne.*—In clusters unless disbudded. The clusters are flat.
- *Stems.*—Short and strong.
- *Form.*—When first open—high center. Permanence—retains its form to the end. Fashion—like a show dahlia.
- *Petalage.*—Very double (many petals and stamens hidden). Number of petals under normal conditions—too numerous to count.
- *Color.*—Center of flower—7.5YR 7/11, strong orange yellow washed with 10YR 8/10, moderate orange yellow. Outer petals—10R 5/11, strong reddish orange washed with 7.5R 5/13, strong reddish orange. Base of petals (singlet)—7.5R 4/11, dark reddish orange. Inside of petals—7.5R 5/13, strong reddish orange washed with 10R 6/12, strong reddish orange. Reverse of petals—2.5Y 8/12, vivid yellow washed with 2.5Y 9/9 brilliant yellow. General tonality from a distance—10R 5/11 strong reddish orange tinted with 10R 6/12, strong reddish orange.
- *Discoloration.*—General tonality at end of: first week—between 10R 6/12, strong reddish orange, and 2.5YR 6/12, strong orange; second week—between 10R 6/12, strong reddish orange and 10R 7/9, strong yellow pink; third week—between 10R 7/9, strong yellowish pink, and 2.5YR 7/10, strong orange.

Petals:

*Texture.*—Thick. Not affected by wet weather. Not affected by hot weather.

*Appearance.*—Satiny inside. Satiny outside.

*Form.*—Oval.

*Arrangement.*—Imbricated.

*Petaloids in center.*—Many.

*Persistence.*—Hang on and dry.

*Fragrance.*—Normal chrysanthemum odor.

*Lastingness.*—On the plant—very long. As cut flower—very long.

Genital organs:

*Stamens, anthers.*—Small. Color—yellow. Arrangement—regular around styles.

*Stamens, filaments.*—Short. Color—lemon yellow.

*Pollen.*—Lemon yellow.

*Styles.*—Columnar.

*Stigmas.*—Yellow.

*Ovaries.*—All enclosed in calyx.

Fruit: Variety is sterile with its own pollen.

*Form.*—Seeds protruding.

*Aspect.*—Rough.

*Color at maturity.*—Russet brown.

*Sepals.*—Caducous.

*Plant*

Form: Bush.

Growth: Compact.

Foliage:

*Leaflets.*—One (alternate).

*Size.*—Large.

*Quantity.*—Abundant.

*Color (new foliage).*—Upper side—light green. Under side—light green.

*Shape.*—Lanceolate.

*Texture.*—Upper side—smooth.

*Ribs and veins*—Ordinary.

*Edge*—Undulated.

*Serration.*—Single.

*Leaf stem.*—Color—green.

*Stipules.*—Medium.

*Disease resistance.*—Immune to diseases.

I claim:

A new and distinct variety of chrysanthemum plant substantially as herein disclosed, characterized as to novelty by the very large, more closed center and strong reddish orange tinted with reddish orange color of its blooms, the very double arrangement of its petals, its short, strong stems, and its better habit and profuse blooms.

No references cited.